(12) United States Patent
McAllister et al.

(10) Patent No.: US 9,011,392 B2
(45) Date of Patent: Apr. 21, 2015

(54) METHODS AND DEVICES FOR DELIVERING AGENTS ACROSS BIOLOGICAL BARRIERS

(75) Inventors: Devin V. McAllister, Shrewsbury, MA (US); Ciro DiMeglio, South Grafton, MA (US)

(73) Assignee: Valeritas, Inc., Bridgewater, NJ (US)

( * ) Notice: Subject to any disclaimer, the term of this patent is extended or adjusted under 35 U.S.C. 154(b) by 0 days.

(21) Appl. No.: 12/414,330

(22) Filed: Mar. 30, 2009

(65) Prior Publication Data

US 2009/0187160 A1 Jul. 23, 2009

Related U.S. Application Data

(62) Division of application No. 11/198,024, filed on Aug. 5, 2005, now abandoned.

(51) Int. Cl.
*A61M 5/32* (2006.01)
*A61B 17/20* (2006.01)
*A61M 37/00* (2006.01)

(52) U.S. Cl.
CPC .............. *A61B 17/205* (2013.01); *A61M 5/322* (2013.01); *A61M 37/0015* (2013.01); *A61M 2037/0023* (2013.01); *A61M 2037/003* (2013.01); *A61M 2037/0053* (2013.01); *A61M 2037/0061* (2013.01)

(58) Field of Classification Search
CPC .................. A61M 2025/0096; A61M 37/0015; A61M 2037/0023; A61M 2037/003; A61M 2037/0038; A61M 2037/0046; A61M 2037/0053; A61M 2037/0061
USPC .......... 604/22, 46, 239, 264, 272–274; 141/2, 141/18
See application file for complete search history.

(56) References Cited

U.S. PATENT DOCUMENTS

| | | | |
|---|---|---|---|
| 3,072,122 | A | 1/1963 | Rosenthal |
| 5,335,670 | A | 8/1994 | Fishman |
| 6,050,988 | A | 4/2000 | Zuck |
| 6,083,196 | A | 7/2000 | Trautman et al. |
| 6,219,574 | B1 | 4/2001 | Cormier et al. |
| 6,230,051 | B1 | 5/2001 | Cormier et al. |
| 6,256,533 | B1 | 7/2001 | Yuzhakov et al. |
| 6,312,612 | B1 | 11/2001 | Sherman et al. |
| 6,322,808 | B1 | 11/2001 | Trautman et al. |
| 6,334,856 | B1 | 1/2002 | Allen et al. |
| 6,379,324 | B1 | 4/2002 | Gartstein et al. |

(Continued)

FOREIGN PATENT DOCUMENTS

| | | |
|---|---|---|
| JP | 2004-520152 | 10/2001 |
| JP | 2002517300 | 6/2002 |

(Continued)

OTHER PUBLICATIONS

Partial European Search Report for Application No. EP 06801016, dated Mar. 25, 2010.

(Continued)

*Primary Examiner* — Matthew F DeSanto

(74) *Attorney, Agent, or Firm* — Lisa M. Warren, Esq.; Morse, Barnes-Brown & Pendleton, P.C.

(57) ABSTRACT

The invention provides for microneedle devices for delivering agents across biological barriers. The microneedles include agent reservoirs integrated into the bodies of the microneedles, themselves.

4 Claims, 14 Drawing Sheets

(56) References Cited

U.S. PATENT DOCUMENTS

| | | |
|---|---|---|
| 6,451,240 B1 | 9/2002 | Sherman et al. |
| 6,471,903 B2 | 10/2002 | Sherman et al. |
| 6,503,231 B1 | 1/2003 | Prausnitz et al. |
| 6,537,264 B1 | 3/2003 | Cormier et al. |
| 6,562,014 B2 | 5/2003 | Lin et al. |
| 6,565,532 B1 | 5/2003 | Yuzhakov et al. |
| 6,611,707 B1 | 8/2003 | Prausnitz et al. |
| 6,652,478 B1 | 11/2003 | Gartstein et al. |
| 6,663,820 B2 * | 12/2003 | Arias et al. .................... 264/496 |
| 6,743,211 B1 * | 6/2004 | Prausnitz et al. ............. 604/239 |
| 6,749,575 B2 | 6/2004 | Matriano et al. |
| 6,881,203 B2 | 4/2005 | Delmore et al. |
| 7,034,854 B2 * | 4/2006 | Cruchon-Dupeyrat et al. ........................ 346/140.1 |
| 2001/0053891 A1 | 12/2001 | Ackley |
| 2002/0020688 A1 | 2/2002 | Sherman et al. |
| 2002/0032415 A1 | 3/2002 | Trautman et al. |
| 2002/0077584 A1 | 6/2002 | Lin et al. |
| 2002/0087182 A1 | 7/2002 | Trautman et al. |
| 2002/0091357 A1 | 7/2002 | Trautman et al. |
| 2002/0102292 A1 | 8/2002 | Cormier et al. |
| 2002/0111600 A1 | 8/2002 | Cormier et al. |
| 2002/0123675 A1 | 9/2002 | Trautman et al. |
| 2002/0128599 A1 | 9/2002 | Cormier et al. |
| 2002/0138049 A1 | 9/2002 | Allen et al. |
| 2002/0168290 A1 | 11/2002 | Yuzhakov et al. |
| 2003/0028087 A1 | 2/2003 | Yuzhakov et al. |
| 2003/0028125 A1 | 2/2003 | Yuzhakov et al. |
| 2003/0045837 A1 | 3/2003 | Delmore et al. |
| 2003/0106809 A1 | 6/2003 | Kermani et al. |
| 2003/0143113 A2 | 7/2003 | Yuzhakov et al. |
| 2003/0207987 A1 | 11/2003 | Leong |
| 2003/0211616 A1 | 11/2003 | Leong |
| 2003/0212344 A1 | 11/2003 | Yuzhakov et al. |
| 2003/0212346 A1 | 11/2003 | Yuzhakov et al. |
| 2004/0049150 A1 * | 3/2004 | Dalton et al. ................. 604/46 |
| 2004/0096455 A1 | 5/2004 | Maa et al. |
| 2004/0106904 A1 | 6/2004 | Gonnelli et al. |
| 2004/0115167 A1 | 6/2004 | Cormier et al. |
| 2004/0181203 A1 | 9/2004 | Cormier et al. |
| 2004/0265365 A1 | 12/2004 | Daddona et al. |
| 2005/0049549 A1 | 3/2005 | Wong et al. |
| 2005/0049625 A1 | 3/2005 | Shaya et al. |
| 2005/0065463 A1 | 3/2005 | Tobinaga et al. |
| 2006/0030811 A1 * | 2/2006 | Wong et al. ...................... 604/46 |
| 2006/0051404 A1 | 3/2006 | Yeshurun et al. |
| 2007/0078414 A1 | 4/2007 | McAllister et al. |
| 2008/0213461 A1 | 9/2008 | Gill et al. |
| 2010/0152701 A1 | 6/2010 | McAllister et al. |

FOREIGN PATENT DOCUMENTS

| | | |
|---|---|---|
| WO | WO 99/64580 | 12/1999 |
| WO | WO 03/024518 A2 | 3/2003 |
| WO | WO 03/048031 A2 | 6/2003 |
| WO | WO 03/053258 A1 | 7/2003 |
| WO | WO 2004/045671 A2 | 6/2004 |
| WO | WO 2004/075971 A1 | 9/2004 |
| WO | WO 2005/018731 | 3/2005 |

OTHER PUBLICATIONS

International Search Report for International Application PCT/US2006/30981, dated Feb. 27, 2007.

Non-Final Office Action for U.S. Appl. No. 11/198,024, dated Dec. 22, 2008.

Final Office Action for U.S. Appl. No. 11/198,024, dated Jun. 23, 2009.

Non-Final Office Action for U.S. Appl. No. 11/198,024, dated Jun. 22, 2010.

Final Office Action for U.S. Appl. No. 11/198,024, dated Mar. 16, 2011.

Non-Final Office Action for U.S. Appl. No. 12/617,566, dated Jun. 24, 2010.

Final Office Action for U.S. Appl. No. 12/617,566, dated Mar. 18, 2011.

European Search Report for Application No. EP 12177394, dated Sep. 12, 2012.

Non-Final Office Action for U.S. Appl. No. 12/617,566, dated Jun. 15, 2012.

Final Office Action for U.S. Appl. No. 12/617,566, dated Jan. 29, 2013.

* cited by examiner

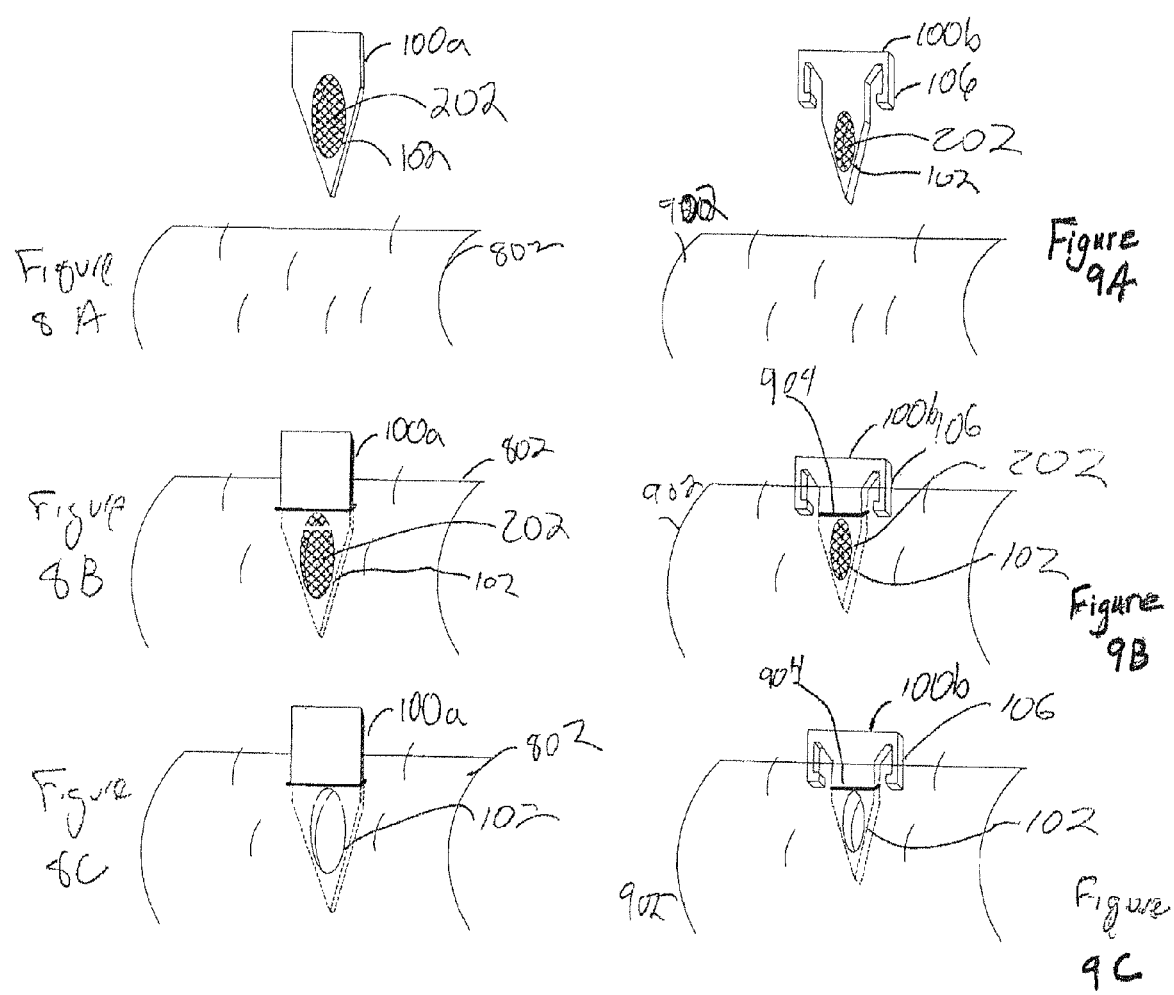

METHODS AND DEVICES FOR DELIVERING AGENTS ACROSS BIOLOGICAL BARRIERS

RELATED APPLICATIONS

This application is a divisional of U.S. application Ser. No. 11/198,024, filed Aug. 5, 2005 now abandoned. The entire teachings of the above application are incorporated herein by reference.

BACKGROUND

Numerous drugs and therapeutic agents have been developed in the battle against disease and illness. However, a frequent therapeutic limitation of these drugs is their delivery: how to transport drugs across biological barriers in the body (e.g., the skin, the oral mucosa, the blood-brain barrier), which normally do not transport drugs at rates that are therapeutically useful.

Drugs are commonly administered orally as pills or capsules. However, many drugs cannot be effectively delivered in this manner due to degradation in the gastrointestinal tract and/or elimination by the liver. Moreover, some drugs cannot effectively diffuse across the intestinal mucosa. Patient compliance may also be a problem, for example, in therapies requiring that pills be taken at particular intervals over a prolonged period.

Another common technique for delivering drugs across a biological barrier is the use of a needle, such as those used with standard syringes or catheters, to transport drugs across (through) the skin. While effective for this purpose, needles generally cause pain; local damage to the skin at the site of insertion; bleeding, which increases the risk of disease transmission; and a wound sufficiently large to be a site of infection.

An alternative delivery technique is the transdermal patch, which usually relies on diffusion of the drug across the skin. However, this method is not useful for many drugs, due to the poor permeability (i.e., effective barrier properties) of the skin. The rate of diffusion depends in part on the size and hydrophilicity of the drug molecules and the concentration gradient across the stratum corneum. Few drugs have the necessary physiochemical properties to be effectively delivered through the skin by passive diffusion. Iontophoresis, electroporation, ultrasound, and heat (so-called active systems) have been used in an attempt to improve the rate of delivery. While providing varying degrees of enhancement, these techniques are not suitable for all types of drugs, failing to provide the desired level of delivery. In some cases, they are also painful and inconvenient or impractical for continuous controlled drug delivery over a period of hours or days. Attempts have been made to design alternative devices for active transfer of drugs through the skin.

Thus, there remains a need for better drug delivery devices, which make smaller incisions, deliver drug with greater efficiency (greater drug delivery per quantity applied) and less variability of drug administration, and/or are easier to use.

SUMMARY

It is therefore an object of the present invention to provide a microneedle device for relatively painless, controlled, safe, convenient delivery of a variety of drugs across one or more biological barriers. In one aspect, the invention relates to a delivery device which includes a microneedle with an integrated agent reservoir. The integrated reservoir may include, for example, an opening extending through the entirety of the width or depth of the needle or a depression in one side of the needle. In such a configuration, when an agent is placed within the integrated reservoir and the microneedle is applied to the biological barrier (e.g., the skin, the oral mucosa barrier, the blood-brain barrier, etc.) of a patient, the agent, being located predominantly within the interior volume of the microneedle, is largely protected from contacting the barrier as the microneedle passes through the barrier. This greatly reduces the loss of the agent cause by contact with the barrier. Such loss can be significant given the small quantity of agent delivered by microneedle technologies and can affect the therapeutic effectiveness of the agent.

In one embodiment, the integrated reservoir encompasses between 20%-50% of the volume of the microneedle. In other embodiments, integrated reservoir encompasses as little as 10% or and as much as 70% of the volume of the first microneedle. The integrated reservoir is filled, in one embodiment with a biologically active agent, such as a drug or a vaccine.

In various embodiments, the microneedle is made of, for example and without limitation, stainless steel, titanium, or a biodegradable polymer. The microneedle can be between 150 and 3000 microns long, and between 10 and 2000 microns wide.

Additional features of the invention include microneedles with depth guards and the use of base elements, which in some embodiments are wider than the microneedles, themselves. The base elements provide for greater structural stability for longer microneedles. The depth guard prevents the wider base elements from entering the biological barrier, which would enlarge the disruption in the barrier caused by the microneedle.

In another embodiment, microneedles are combined into arrays. The arrays of microneedles allow for administration of larger volumes of agent and for concurrent administration of multiple agents. The microneedles in the array may be attached to a substrate.

In another aspect, the invention relates to manufacturing the delivery devices described above. The method of manufacture may include dipping the microneedle into a solution containing the agent. In an alternative embodiment, a predetermined volume of the agent is dispensed into the integrated reservoir.

In another aspect, the invention relates to methods of administering an agent across a biological barrier. The administration method includes applying one of the microneedle devices described above against a biological barrier, thereby puncturing the barrier and positioning the integrated reservoir beyond the barrier. In one embodiment, the method includes providing a plurality of microneedles coupled to a substrate. At least one of the microneedles includes an opening which defines an integrated reservoir. The reservoir is filled with an agent. The plurality of microneedles are applied against the skin of a patient, puncturing the skin and positioning the integrated reservoir beneath the surface of the skin. The puncture depth is limited by a depth guard coupled to at least one of the microneedles.

BRIEF DESCRIPTION OF THE FIGURES

The invention may be better understood from the following illustrative description with reference to the following drawings.

FIGS. 8 and 9 illustrate methods of administering an agent transdermally to a patient according to two embodiments of the invention.

DESCRIPTION OF ILLUSTRATIVE EMBODIMENTS

Figure 1A:
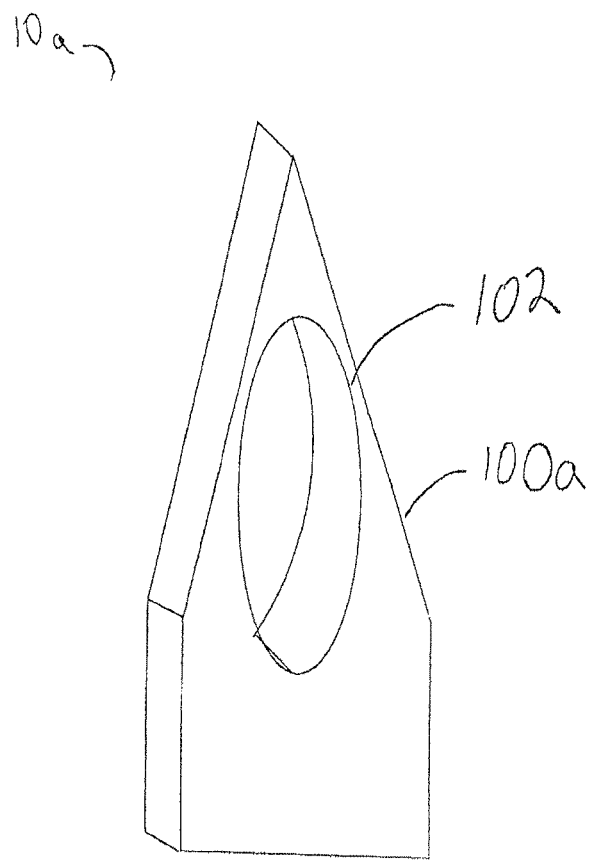
FIGS. 1A through 1D depict microneedles with integrated drug reservoirs according to several illustrative embodiments of the invention.

Throughout the description below reference to ranges of values are intended to refer to the specified range, and any smaller range, or single value within that range. Thus, a range of 1 to 10 refers, for example, to the ranges 1 to 10, 3 to 7, or 5. In addition, like reference numerals refer to like elements.

The devices disclosed herein are useful in transport of material into or across biological barriers including the skin (or parts thereof); the blood-brain barrier; mucosal tissue (e.g., oral, nasal, ocular, vaginal, urethral, gastrointestinal, respiratory); blood vessels; lymphatic vessels; or cell membranes (e.g., for the introduction of material into the interior of a cell or cells). The biological barriers could be in humans or other types of animals, as well as in plants, insects, or other organisms, and embryos.

For internal tissues, application of the microneedle devices can be achieved with the aid of a catheter or laparoscope. For certain applications, such as for drug delivery to an internal tissue, the devices can be surgically implanted.

Skin is a biological barrier of particular use with the microneedle device disclosed herein. However, skin is only one example of a biological barrier. It will be understood that any biological barrier can be substituted for "skin" throughout.

Specifically with respect to skin, the stratum corneum is the outer layer, generally between 10 and 50 cells, or between 10 and 20 µm thick. Unlike other tissue in the body, the stratum corneum contains "cells" (called keratinocytes) filled with bundles of cross-linked keratin and keratohyalin surrounded by an extracellular matrix of lipids. It is this structure that is believed to give skin its barrier properties, which prevents therapeutic transdermal administration of many drugs.

Below the stratum corneum is the viable epidermis, which is between 50 and 100 µm thick. The viable epidermis contains no blood vessels, and it exchanges metabolites by diffusion to and from the dermis. Beneath the viable epidermis is the dermis, which is between 1 and 3 mm thick and contains blood vessels, lymphatics, and nerves.

Figure 1B:
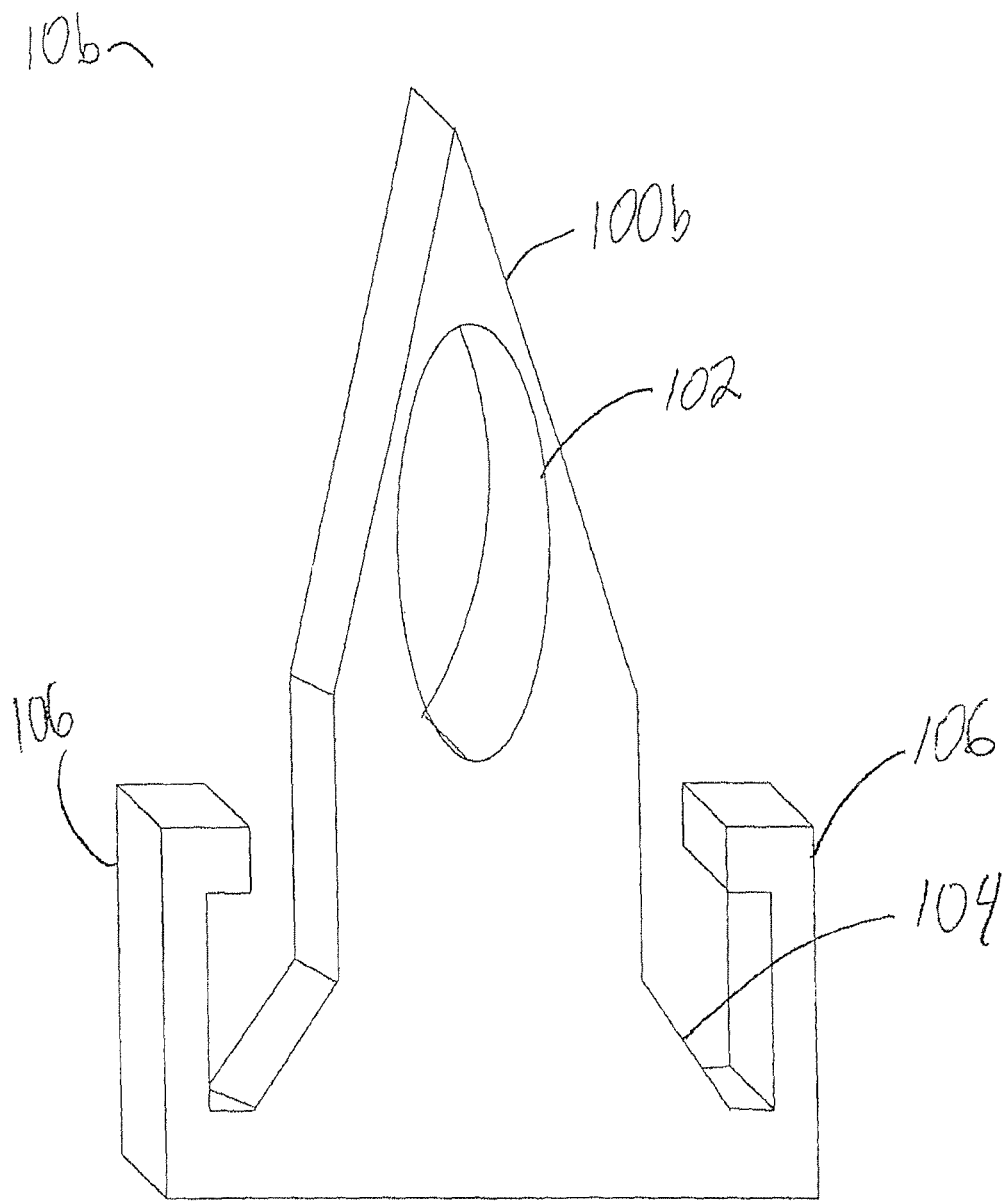
Figure 1C:
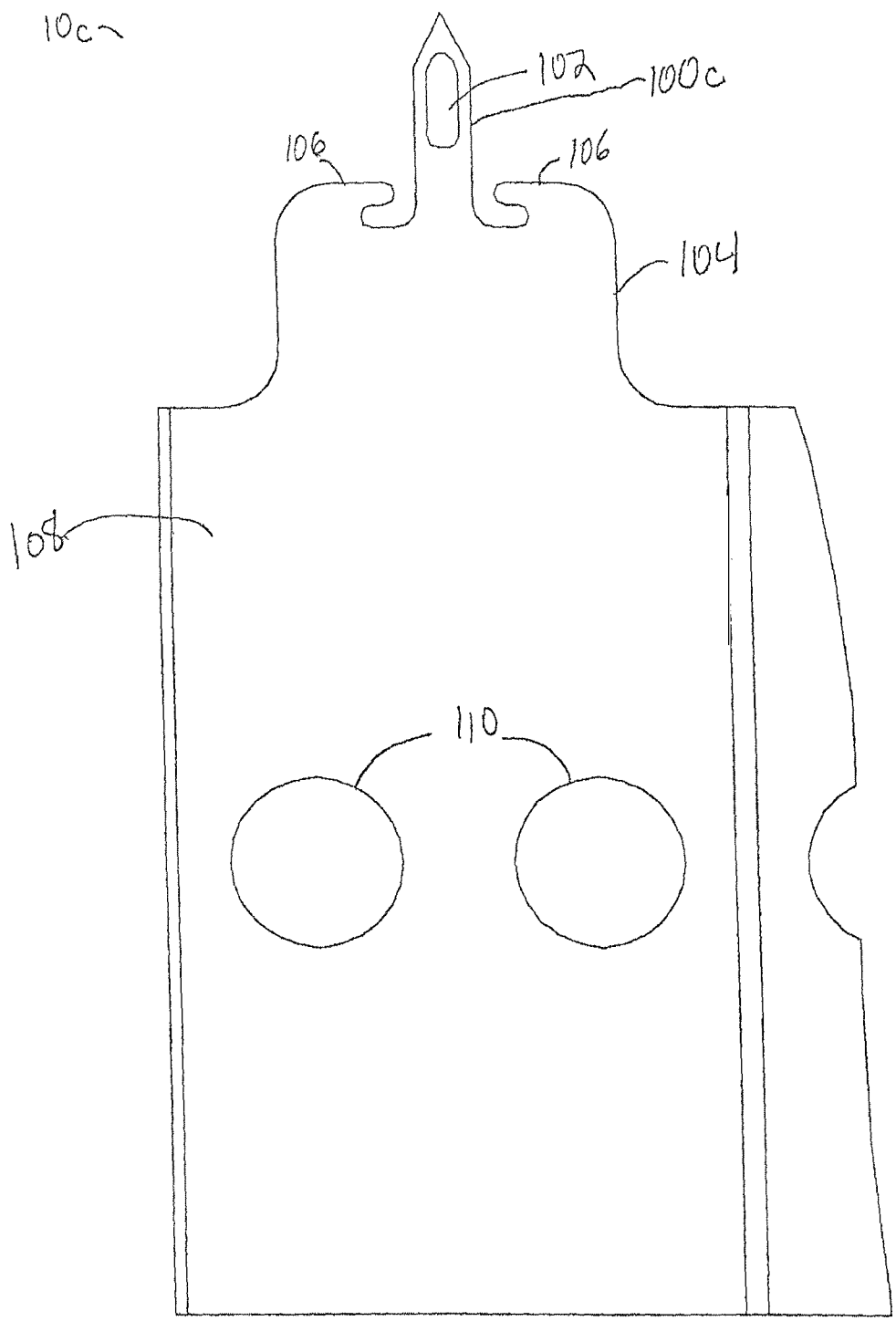

FIGS. 1A-C depict three versions of agent delivery devices (generally referred to as agent delivery devices 10) for delivering agents across biological barriers. Each agent delivery device 10 includes a microneedle (generally referred to as microneedle 100) with integrated agent reservoirs 102 according to illustrative embodiments of the invention. Microneedles 100 include microprotrusions, microabraders, microblades, and other elements on the submicron to millimeter scale used to pierce, cut, or otherwise disrupt the surface of a biological barrier. The microneedle 100 can be constructed from a variety of materials, including metals, ceramics, semiconductors, organics, polymers (e.g., biodegradable polymers), and composites. Preferred materials of construction include medical grade stainless steel, gold, titanium, nickel, iron, gold, tin, chromium, copper, alloys of these or other metals, silicon, silicon dioxide, and polymers. Representative biodegradable polymers include polymers of hydroxy acids such as lactic acid and glycolic acid polylactide, polyglycolide, polylactide-co-glycolide, and copolymers with PEG, polyanhydrides, poly(ortho)esters, polyurethanes, poly(butyric acid), poly(valeric acid), and poly (lactide-co-caprolactone). Representative non-biodegradable polymers include polycarbonate, polymethacrylic acid, ethylenevinyl acetate, polytetrafluorethylene (TEFLON™), and polyesters.

Generally, a microneedle 100 should have the mechanical strength to remain intact for delivery of an agent, while being inserted into the barrier, while remaining in place for up to a number of days, and while being removed. In embodiments where the microneedle 100 is formed of biodegradable polymers, however, this mechanical requirement is less stringent, since the microneedle 100 or the tip thereof can break off, for example in the skin, and will biodegrade. Therefore, biodegradable microneedles 100 can provide an increased level of safety, as compared to nonbiodegradable ones. Nonetheless, even a biodegradable microneedle 100 still needs to remain intact at least long enough for the microneedle 100 to serve its intended purpose (e.g, its delivery function). The microneedle 100 should preferably be sterilizable using standard methods.

In general, one benefit of delivering an agent via a microneedle 100 is that while the microneedle 100 disrupts a patient's skin, thereby providing access to the blood flow of a patient, it does not disrupt the skin deep enough to generate a response from the patient's nerves. Thus agent delivery via a microneedle 100 typically is less painful than standard injection delivery devices. To this end, the height (or length) of the microneedle 100 generally is between about 100 µm and about 3 mm. In transdermal applications, the "insertion depth" of the microneedle 100 is preferably between about 100 µm and about 1 mm, so that insertion of the microneedle 100 into the skin does not penetrate through the lower dermis. In such applications, the actual length of the microneedle 100 may be longer, since some portion of the microneedle 100 distal the tip may not be inserted into the skin; the uninserted length depends on the particular device design and configuration.

In order to reduce injury and the risk of infection to the patient, the microneedle 100 is formed to be between 10 µm and about 2 mm wide, preferably between 100 and 300 µm wide. A microneedle 100 will be generally planar, cylindrical, conical, or rectangular in shape, though other polygonal and irregular shapes are also suitable. The distal end of the microneedle 100 preferably tapers to a point.

The agent delivery device 10*a* illustrated in FIG. 1A, includes microneedle 100*a*. Microneedle 100*a* includes an integrated reservoir 102 for holding agents to be delivered across a biological barrier, such as the skin. The integrated reservoir 102 consists of an opening that passes through a side of the microneedle 100*a*. The integrated reservoir 102 encompasses a substantial portion of the volume of the microneedle 100*a*. For example, the reservoir 102 encompasses between 10% and 70% of the volume of the microneedle 100*a*. In other configurations, the integrated reservoir 102 encompasses between 20 and 50% of the volume of the microneedle 100*a*. Thus, the exposed surface area of any agent stored in the integrated reservoir 102 is relatively low in relation to the total volume of the stored agent. The integrated reservoir 102 is contained wholly within the physical bounds of the microneedle 100*a*. The integrated reservoir 102 can take on virtually any shape, whether it be polygonal, irregular, circular, or elliptical.

FIG. 1B depicts a second agent delivery device 10*b* for delivering agents across biological barriers. The delivery device 10*b* includes a microneedle 100*b* with an integrated reservoir 102 according to a second embodiment of the invention. The microneedle 100*b* is coupled to a base element 104. The base element 104 can be wider than the microneedle 100*b* to provide additional strength and stability.

To prevent the base element 104 from widening the wound in a patient's skin during insertion, the delivery device 10*b* includes a depth guard 106. The depth guard 106 includes a rigid member that extends from the base element 104 toward the distal end of the microneedle 100*b* to a point beyond the base element 104. In an alternative embodiment, the depth guard 106 extends out directly from the microneedle 100*b*, substantially perpendicular to the length of the microneedle 100*b*. In both embodiments, upon application of the microneedle 100*b* to the skin of a patient, the depth guard 106 acts as a barrier and prevents the microneedle 100*b* from being inserted so deep within the skin that the wider base element 104 further disrupts the skin surface. In embodiments in which the base element 104 is not substantially wider than the microneedle 100*b*, the depth guard 106 prevents the microneedle 100*b* from penetrating too deeply.

FIG. 1C depicts a third illustrative embodiment of a delivery device 10*c* according to an illustrative embodiment of the invention. Delivery device 10*c* includes microneedle 100*c* with an integrated reservoir 102. In addition to the features of the delivery devices 10*a* and 10*b* depicted in FIGS. 1A-1B, the delivery device 10*c* includes a substrate 108 to which the base element 104 is coupled. In the illustrative embodiment, the substrate 108 is formed integrally with the base element 104, microneedle 100*c*, and depth guard 106. The substrate can be, for example, between 300 μm-500 μm wide and between about 400 μm and about 1 mm long. As shown, the substrate 108 is generally parallel to the base element 104 and microneedle 100*c*, though in other embodiments, the substrate 108 is generally perpendicular to, or at an angle to the base element 104 and substrate 108. The substrate 108 includes two alignment holes 110 for aligning a plurality of microneedles 100*c* into an array. The alignment holes 110 can be, for example, spaced between about 100 μm to about 300 μm apart, and be between about 50 μm to about 200 μm in diameter.

Figure 1D:
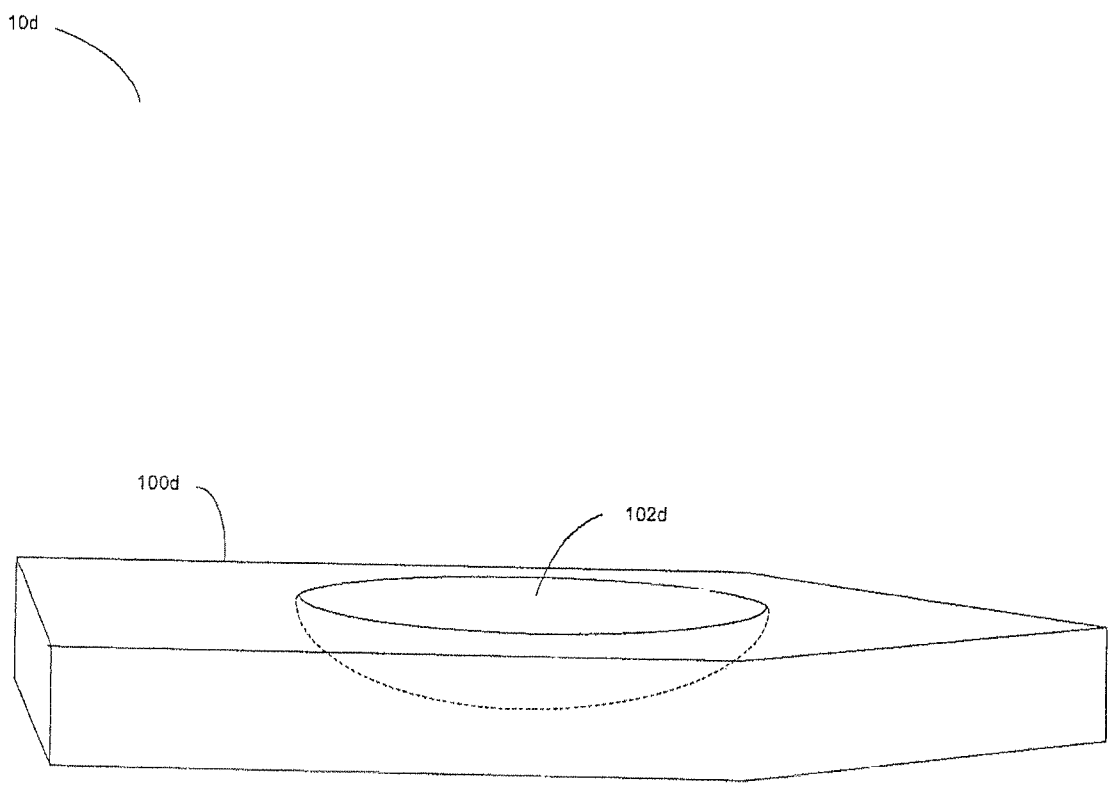

In another embodiment of the delivery device 10*d*, depicted in FIG. 1D, the microneedle 100*d* includes an integrated reservoir 102*d*, which does not pass through the entirety of the side of the microneedle 100*d*. Instead, the integrated reservoir 102*d* is formed by creating a depression into one or more sides of the microneedle 100*d* into which an agent can be placed. As with the version of the integrated reservoir 102 in which the reservoir passes through the entirety of a side of a microneedle 100*a*, described above in relation to FIG. 1A, the depression integrated reservoir 102*d* preferably takes up a substantial portion of the volume of the microneedle 100*d*. The integrated reservoir 102*d* can take on virtually any shape, whether it be polygonal, irregular, circular, or elliptical.

Figure 2A:
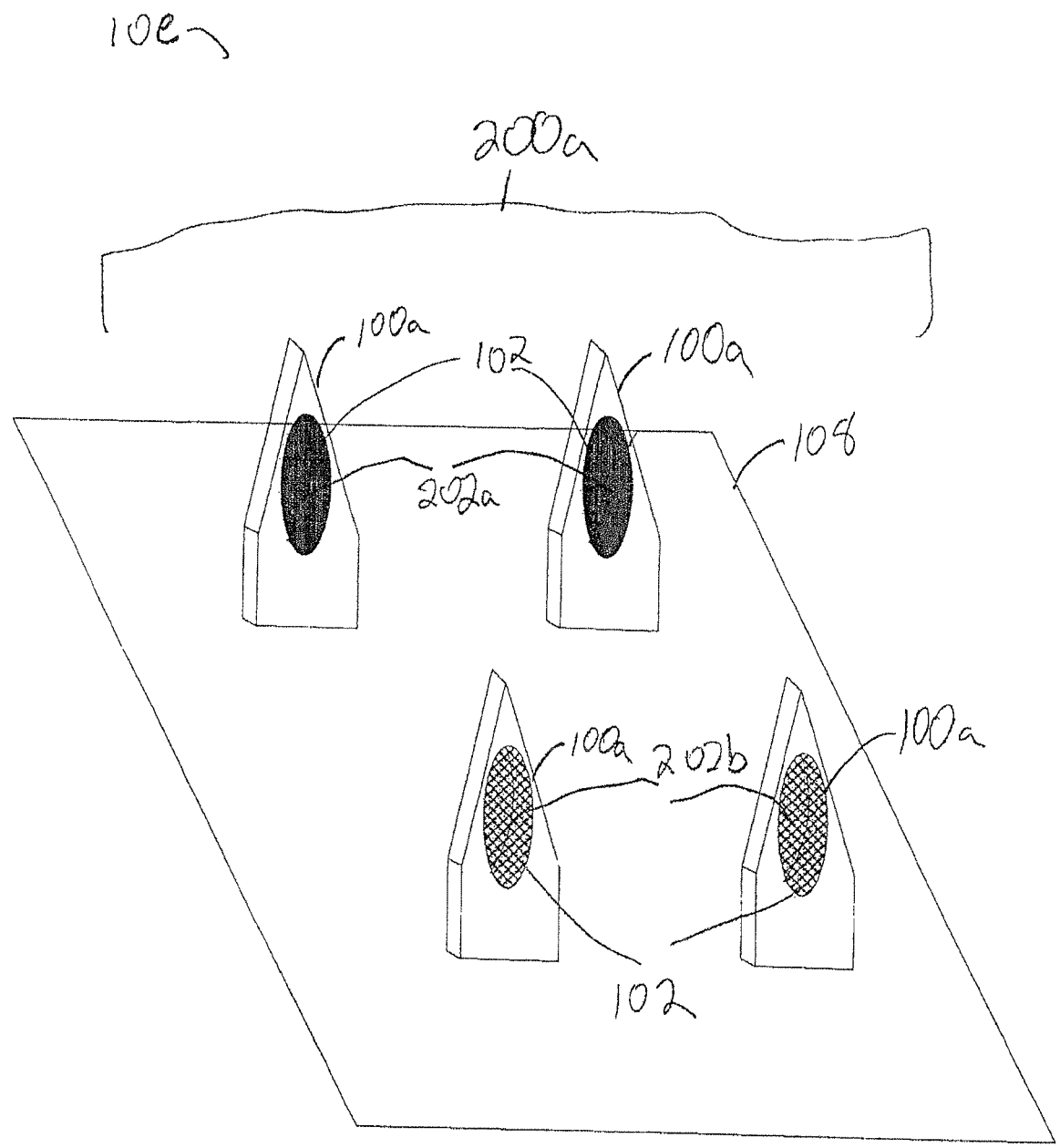
FIGS. 2A through 2C depict arrays of microneedles with integrated drug reservoirs according to illustrative embodiments of the invention.
Figure 2B:
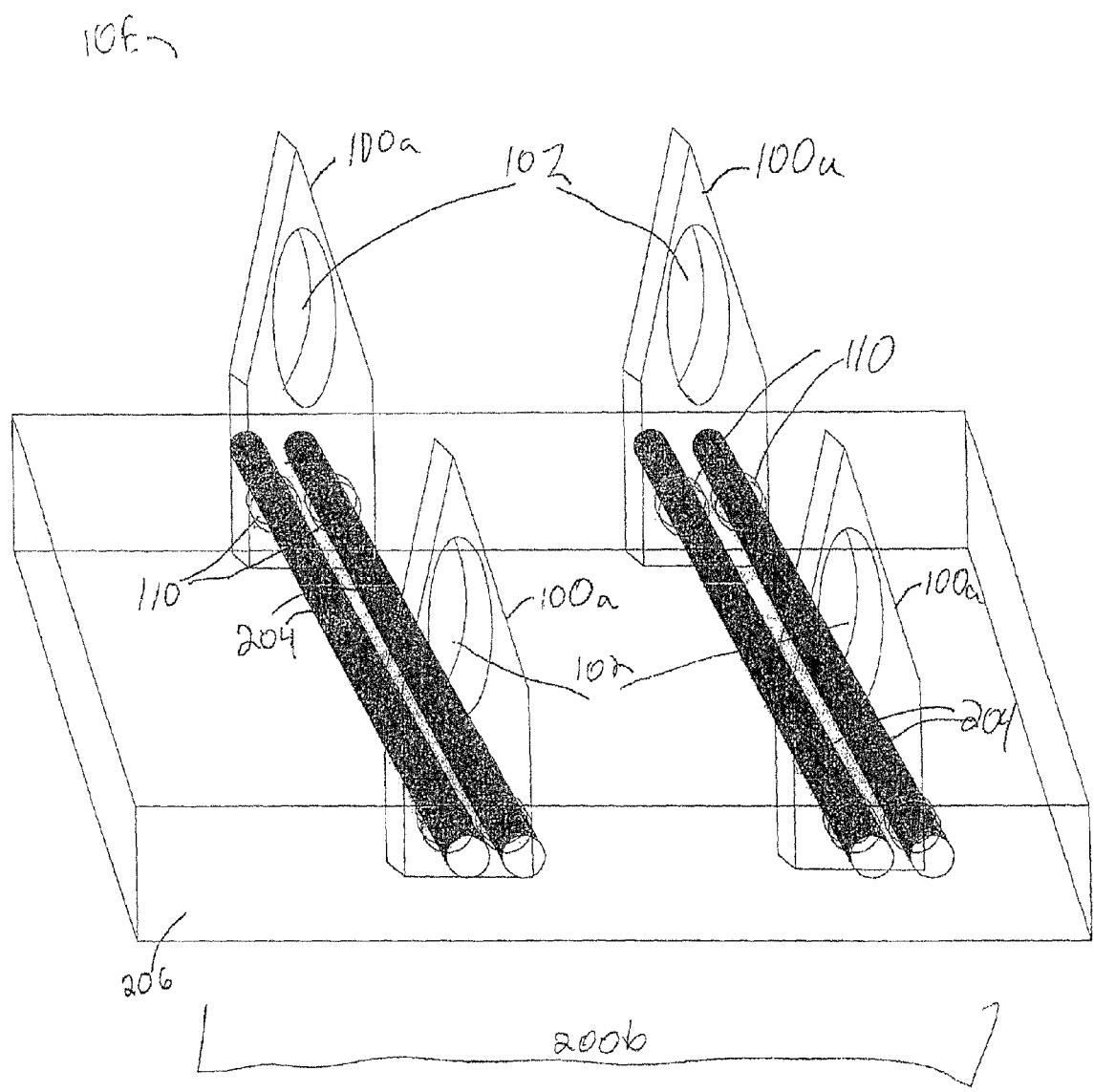
Figure 2C:
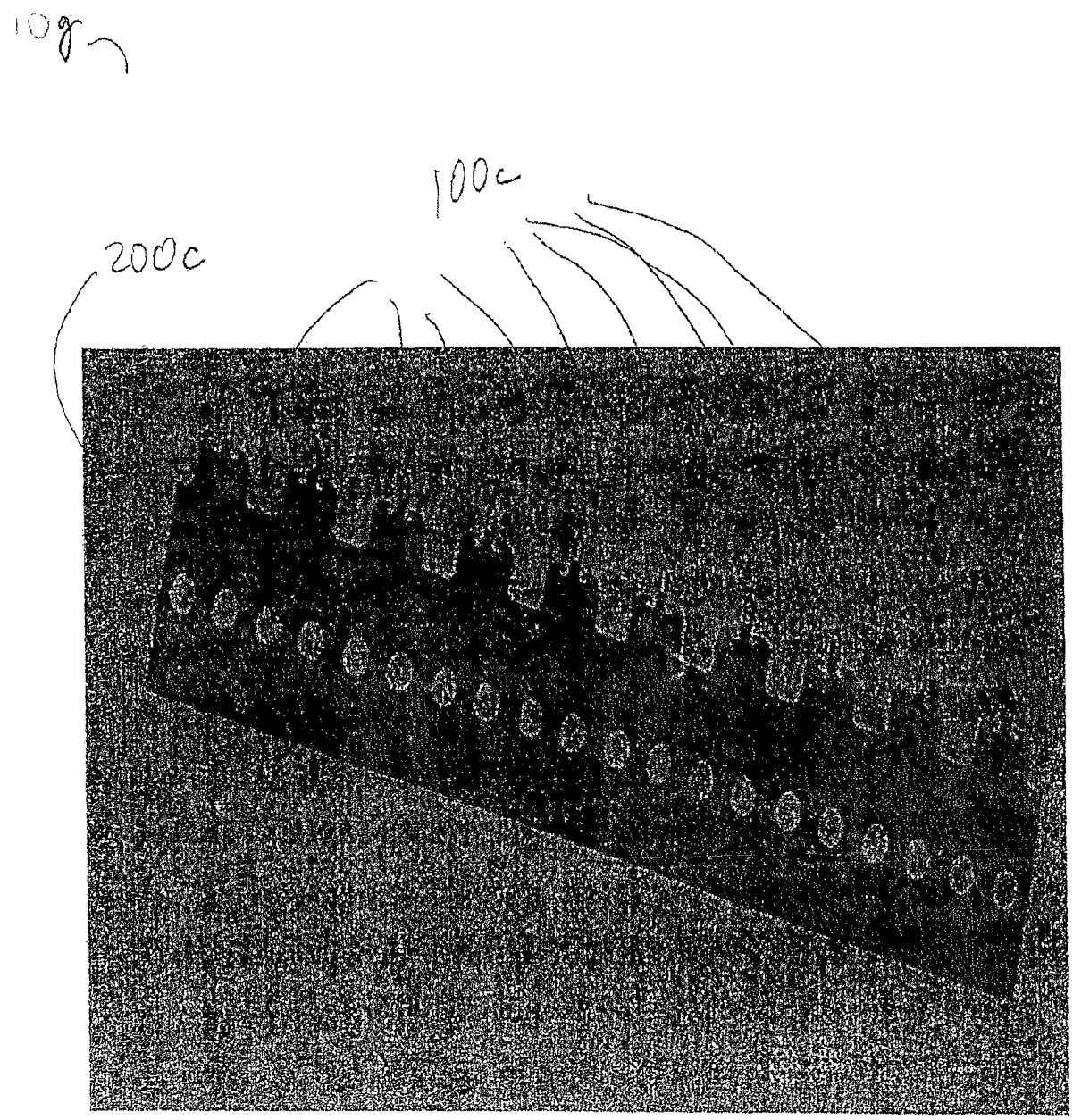

FIGS. 2A-2C illustrate arrays of microneedles according to three illustrative embodiments of the invention. Microneedle arrays (generally microneedle arrays 200) are useful, for example and without limitation, in at least the three following circumstances: 1) if the reservoir 102 of a single microneedle 100 may not be able to hold a sufficient volume of an agent to be effective; 2) if it desired to deliver the agent or agents to a greater surface area of a biological barrier; and 3) if multiple agents are to be administered concurrently and the multiple agents are not sufficiently compatible to store or administer in a single microneedle 100 integrated reservoir 102.

FIG. 2A depicts a delivery device 10*e* including a two-dimensional microneedle array 200*a* according to an illustrative embodiment of the invention. The two-dimensional microneedle array 200*a* includes four microneedles 100*a*, as described in relation to FIG. 1A. The inclusion of only four microneedles 100*a* in the two-dimensional microneedle array 200*a* is for illustrative purposes only. The two-dimensional microneedle array 200*a* may include a smaller or larger number of microneedles 100*a*. For example, the two-dimensional microneedle array 200*a* may include as few as three microneedles 100*a*. The dimensionality of the microneedle array 200*a* refers to the geometric relationship among the microneedles 100*a* in the array, and thus, two microneedles by definition could only form a one dimensional array. The two-dimensional microneedle array can include as many as sixteen microneedles 100*a*, or more. Other microneedle 100 implementations, for example and without limitation, microneedles 100*b*-100*d*, may be incorporated into the two-dimensional microneedle array 200*a*.

The microneedles 100*a* in the two-dimensional microneedle array 200*a* are attached to a substrate 108. The microneedles 100*a* may be integrally formed with the substrate 108 or they may be physically attached, for example with an adhesive, to the substrate 108. In the two-dimensional array 200*a*, the substrate 108 serves as a depth guard 106. In other implementations, one or more of the microneedles 100*a* on the two-dimensional array 200*a* include independent depth guards 106.

In the two-dimensional microneedle array 200*a* depicted in FIG. 2A, two of the microneedles 100*a* include a first agent 202*a* stored in their corresponding integrated reservoirs 102 and two of the microneedles 100*a* include a different agent 202*b* (agents will be referred to hereinafter generally as agents 202).

Two-dimensional microneedle array 200*a* may also include a feature in which the substrate 108 is coated with an adhesive for adhering to the patient's skin. The adhesive keeps the integrated reservoirs 102 of the microneedles 100 beneath the skin for extended periods of time, for example, to allow for gradual absorption of agents stored in the reservoir 102.

FIG. 2B depicts a second illustrative embodiment of a delivery device 10*f* having a two-dimensional microneedle array 200*b*. Two-dimensional microneedle array 200*b* includes four microneedles 100*d*. Microneedles 100*d* resemble microneedles 100*a* with the addition of alignment holes 110, as previously depicted in microneedle 100*c*. In this two-dimensional array 200b, alignment elements 204 pass through the alignment holes 110 of the microneedles 100d and into base structure 206. Spacers 208 can be placed on the alignment elements between the microneedles 100c to keep them apart and firmly in place.

FIG. 2C depicts a delivery device 10g including a one-dimensional microneedle array 200c according to an illustrative embodiment of the invention. The one-dimensional microneedle array 200c includes ten microneedles 100c. The one-dimensional microneedle array 200c may have fewer than ten microneedles 100c (as few as two) or it can include additional microneedles 100c. The one-dimensional microneedle array 200c may be formed by manufacturing a single integrated set of microneedles, or each microneedle 100c may be formed independently and then joined together. The microneedles 100c can be joined using, for example, adhesives, bonding, or alignment elements 204.

Figure 3:
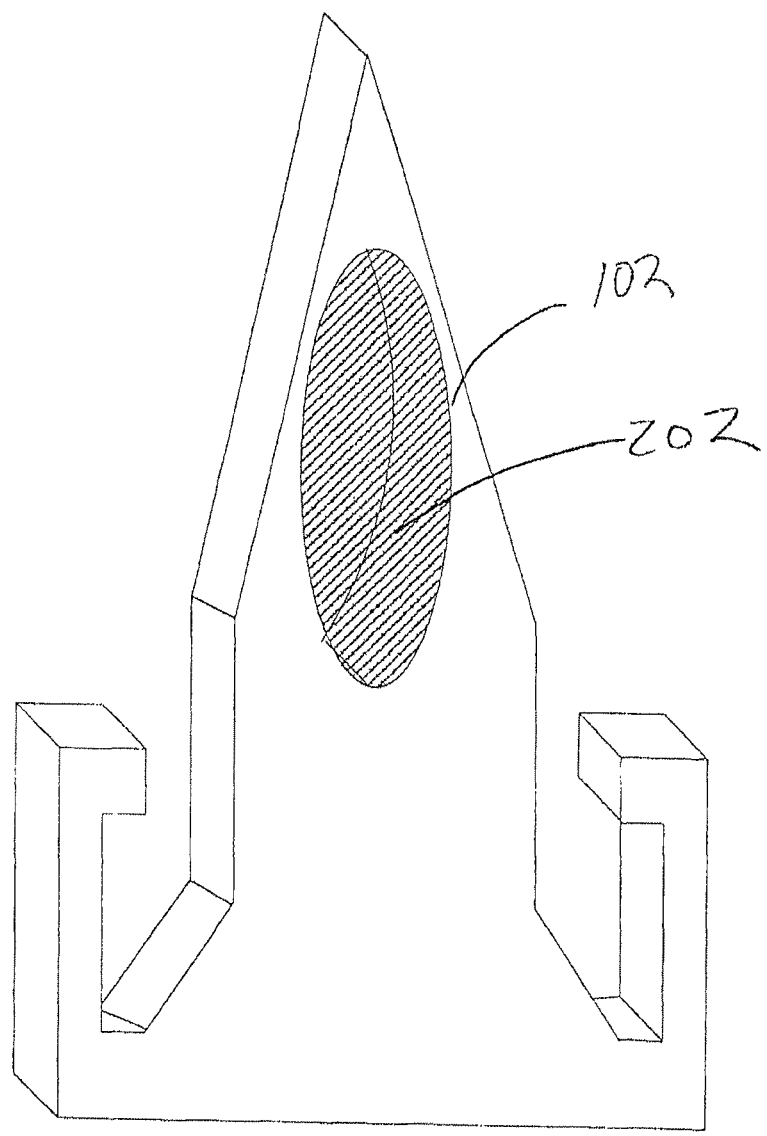
FIG. 3 depicts a microneedle with an integrated drug reservoir which is filled with an agent according to an illustrative embodiment of the invention.

FIG. 3 depicts delivery device 10b depicted in FIG. 1B having an agent 202 place in the integrated reservoir 102. The term agent refers to a single agent 202 or a combination of several agents 202. The agents 202 may be biologically active or biologically inactive. Sample agents 202 include, without limitation, drugs, vaccines, allergens, antigens, excipients, anti-coagulants, surfactants, radiological dyes or markers, toxins, or any other agent, compound or substance suitable for introduction into a biological barrier. As stored, the agents 202 may be, for example, dry (e.g., a film), or in a semi-solid gel.

One class of agents 202 includes therapeutic agents in all the major therapeutic areas including, but not limited to, anti-infectives, such as antibiotics and antiviral agents; analgesics, including fentanyl, sufentanil, remifentanil, buprenorphine and analgesic combinations; anesthetics; anorexics; antiarthritics; antiasthmatic agents such as terbutaline; anticonvulsants; antidepressants; antidiabetic agents; antidiarrheals; antihistamines; anti-inflammatory agents; antimigraine preparations; antimotion sickness preparations such as scopolamine and ondansetron; antinauseants; antineoplastics; antiparkinsonism drugs; antipruritics; antipsychotics; antipyretics; antispasmodics, including gastrointestinal and urinary; anticholinergics; sympathomimetrics; xanthine derivatives; cardiovascular preparations, including calcium channel blockers such as nifedipine; beta blockers; beta-agonists such as dobutamine and ritodrine; antiarrythmics; antihypertensives such as atenolol; ACE inhibitors such as ranitidine; diuretics; vasodilators, including general, coronary, peripheral, and cerebral; central nervous system stimulants; cough and cold preparations; decongestants; diagnostics; hormones such as parathyroid hormone; hypnotics; immunosuppressants; muscle relaxants; parasympatholytics; parasympathomimetrics; prostaglandins; proteins; peptides; psychostimulants; sedatives; and tranquilizers. These agents may take the form of peptides, proteins, carbohydrates (including monosaccharides, oligosaccharides, and polysaccharides), nucleoproteins, mucoproteins, lipoproteins, glycoproteins, nucleic acid molecules (including any form of DNA such as cDNA, RNA, or a fragment thereof, oligonucleotides, and genes), nucleotides, nucleosides, lipids, biologically active organic or inorganic molecules, or combinations thereof.

Further specific examples of agents 202 include, without limitation, growth hormone release hormone (GHRH), growth hormone release factor (GHRF), insulin, insultropin, calcitonin, octreotide, endorphin, TRN, NT-36 (chemical name: N-[[(s)-4-oxo-2-azetidinyl]carbonyl]-L-histidyl-L-p-rolinamide), liprecin, pituitary hormones (e.g., HGH, HMG, desmopressin acetate, etc), follicle luteoids, aANF, growth factors such as growth factor releasing factor (GFRF), bMSH, GH, somatostatin, bradykinin, somatotropin, platelet-derived growth factor releasing factor, asparaginase, bleomycin sulfate, chymopapain, cholecystokinin, chorionic gonadotropin, erythropoietin, epoprostenol (platelet aggregation inhibitor), gluagon, HCG, hirulog, hyaluronidase, interferon alpha, interferon beta, interferon gamma, interleukins, interleukin-10 (IL-10), erythropoietin (EPO), granulocyte macrophage colony stimulating factor (GM-C SF), granulocyte colony stimulating factor (G-CSF), glucagon, leutinizing hormone releasing hormone (LHRH), LHRH analogs (such as goserelin, leuprolide, buserelin, triptorelin, gonadorelin, and napfarelin, menotropins (urofollitropin (FSH) and LH)), oxytocin, streptokinase, tissue plasminogen activator, urokinase, vasopressin, deamino [Val4, D-Arg8] arginine vasopressin, desmopressin, corticotropin (ACTH), ACTH analogs such as ACTH (1-24), ANP, ANP clearance inhibitors, angiotensin II antagonists, antidiuretic hormone agonists, bradykinin antagonists, ceredase, CSI's, calcitonin gene related peptide (CGRP), enkephalins, FAB fragments, IgE peptide suppressors, IGF-1, neurotrophic factors, colony stimulating factors, parathyroid hormone and agonists, parathyroid hormone antagonists, parathyroid hormone (PTH), PTH analogs such as PTH (1-34), prostaglandin antagonists, pentigetide, protein C, protein S, renin inhibitors, thymosin alpha-1, thrombolytics, TNF, vasopressin antagonists analogs, alpha-1 antitrypsin (recombinant), and TGF-beta.

The biologically active agents 202 can also be in various forms, such as free bases, acids, charged or uncharged molecules, components of molecular complexes or nonirritating, pharmacologically acceptable salts. Further, simple derivatives of the active agents 202 (such as ethers, esters, amides, etc.), which are easily hydrolyzed at body pH, enzymes, etc., can be employed.

Additional agents 202 may be stored in the same integrated reservoir 102 as a therapeutic agent 202, or they may be stored in integrated reservoirs 102 integrated into separate microneedles 100. For example, the integrated reservoir 102 may contain a viscosity enhancing agent 202 such as maleic acid, malic acid, malonic acid, tartaric acid, adipic acid, citraconic acid, fumaric acid, glutaric acid, itaconic acid, meglutol, mesaconic acid, succinic acid, citramalic acid, tartronic acid, citric acid, tricarballylic acid, ethylenediaminetetraacetic acid, aspartic acid, glutamic acid, carbonic acid, sulfuric acid, phosphoric acid, hydrochloric acid, hydrobromic acid, nitric acid, sulfuric acid, benzene sulfonic acid, methane sulfonic acid, glycolic acid, gluconic acid, glucuronic acid, lactic acid, pyruvic acid, tartronic acid, propionic acid, pentanoic acid, carbonic acid, adipic acid, citraconic acid, and levulinic acid.

Additional potential agents 202 include surfactants, such as zwitterionic, amphoteric, cationic, anionic, or nonionic, including, without limitation, sodium lauroamphoacetate, sodium dodecyl sulfate (SDS), cetylpyridinium chloride (CPC), dodecyltrimethyl ammonium chloride (TMAC), benzalkonium, chloride, polysorbates such as Tween 20 and Tween 80, other sorbitan derivatives, such as sorbitan laurate, and alkoxylated alcohols, such as laureth-4.

Still other useful agents 202 include polymeric materials or polymers that have amphiphilic properties, for example and without, cellulose derivatives, such as hydroxyethylcellulose (HEC), hydroxypropylmethylcellulose (HPMC), hydroxypropylcellulose (HPC), methylcellulose (MC), hydroxyethylmethylcellulose (HEMC), or ethylhydroxy-ethylcellulose (EHEC), as well as pluronics.

Further agents 202 compatible for use in the integrated reservoir 102 include biocompatible carriers, which include, without limitation, human albumin, bioengineered human albumin, polyglutamic acid, polyaspartic acid, polyhistidine, pentosan polysulfate, polyamino acids, sucrose, trehalose, melezitose, raffinose and stachyose.

Stabilizing agents 202, which can comprise, without limitation, a non-reducing sugar, a polysaccharide or a reducing sugar, may be stored in the integrated reservoir 102. Suitable non-reducing sugars for use in the methods and compositions of the invention include, for example, sucrose, trehalose, stachyose, or raffinose. Suitable polysaccharides for use in the methods and compositions of the invention include, for example, dextran, soluble starch, dextrin, and insulin. Suitable reducing sugars for use in the methods and compositions of the invention include, for example, monosaccharides such as, for example, apiose, arabinose, lyxose, ribose, xylose, digitoxose, fucose, quercitol, quinovose, rhamnose, allose, altrose, fructose, galactose, glucose, gulose, hamamelose, idose, mannose, tagatose, and the like; and disaccharides such as, for example, primeverose, vicianose, rutinose, scillabiose, cellobiose, gentiobiose, lactose, lactulose, maltose, melibiose, sophorose, and turanose, and the like.

Other agents 202 include "pathway patency modulators", which can comprise, without limitation, osmotic agents 202 (e.g., sodium chloride), zwitterionic compounds (e.g., amino acids), and anti-inflammatory agents, such as betamethasone 21-phosphate disodium salt, triamcinolone acetonide 21-disodium phosphate, hydrocortamate hydrochloride, hydrocortisone 21-phosphate disodium salt, methylprednisolone 21-phosphate disodium salt, methylprednisolone 21-succinaate sodium salt, paramethasone disodium phosphate and prednisolone 21-succinate sodium salt, and anticoagulants, such as citric acid, citrate salts (e.g., sodium citrate), dextrin sulfate sodium, aspirin and EDTA.

In yet another embodiment of the invention, the integrated reservoir 102 includes a solubilising/complexing agent 202, for example, alpha-cyclodextrin, beta-cyclodextrin, gamma-cyclodextrin, glucosyl-alpha-cyclodextrin, maltosyl-alpha-cyclodextrin, glucosyl-beta-cyclodextrin, maltosyl-beta-cyclodextrin, hydroxypropyl beta-cyclodextrin, 2-hydroxypropyl-beta-cyclodextrin, 2-hydroxypropyl-gamma-cyclodextrin, hydroxyethyl-beta-cyclodextrin, methyl-beta-cyclodextrin, sulfobutylether-alpha-cyclodextrin, sulfobutylether-beta-cyclodextrin, sulfobutylether7 beta-cyclodextrin, and sulfobutylether-gamma-cyclodextrin.

Additional useful agents 202 include non-aqueous solvents, such as ethanol, isopropanol, methanol, propanol, butanol, propylene glycol, dimethysulfoxide, glycerin, N,N-dimethylformamide and polyethylene glycol 400.

In order to facilitate filling of the integrated reservoir 102, hydrophilic compounds can be applied to the surfaces of the microneedle 100 defining the integrated reservoir 102. The hydrophilic compound can be selected from the following group: hydroxyethyl starch, dextran, poly(vinyl alcohol), poly(ethylene oxide), poly(2-hydroxyethylmethacrylate), poly(n-vinyl pyrolidone), polyethylene glycol and mixtures thereof, and like polymers. A hydrophobic compound, such as TEFLON™, silicon or other low energy material, can be applied to the remainder of the microneedle 100.

Microneedles 100, as depicted in FIGS. 1A-1C, can be formed using a variety of microfabrication techniques known in the art. For example, the microneedles 100 can be fabricated using lithography; etching techniques, such as wet chemical, dry, and photoresist removal; thermal oxidation of silicon; electroplating and electroless plating; diffusion processes, such as boron, phosphorus, arsenic, and antimony diffusion; ion implantation; film deposition, such as evaporation (filament, electron beam, flash, and shadowing and step coverage), sputtering, chemical vapor deposition (CVD), epitaxy (vapor phase, liquid phase, and molecular beam), electroplating, screen printing, and lamination. See generally Jaeger, Introduction to Microelectronic Fabrication (Addison-Wesley Publishing Co., Reading Mass. 1988); Runyan, et al., Semiconductor Integrated Circuit Processing Technology (Addison-Wesley Publishing Co., Reading Mass. 1990); Proceedings of the IEEE Micro Electro Mechanical Systems Conference 1987-1998; Rai-Choudhury, ed., Handbook of Microlithography. Micromachining & Microfabrication (SPIE Optical Engineering Press, Bellingham, Wash. 1997).

More particularly, FIGS. 4A-6C depict specific methods of forming microneedles 100 with integrated agent reservoirs 102 as described in relation to FIGS. 1A-C.

Figure 4A:
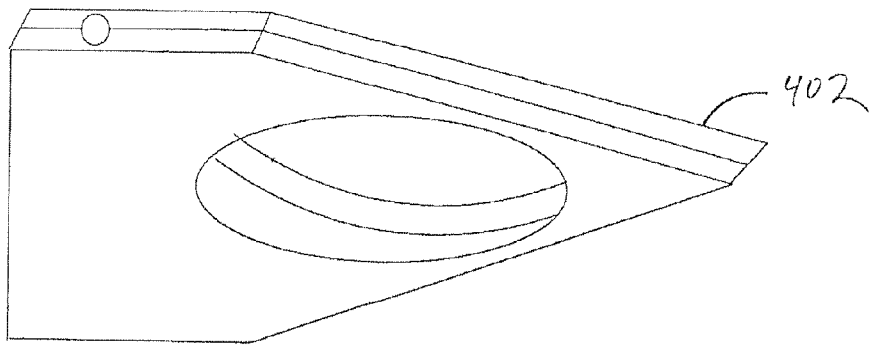
FIGS. 4A through 4C depict a method of forming a microneedle with an integrated drug reservoir using injection molding according to an illustrative embodiment of the invention.
Figure 4B:
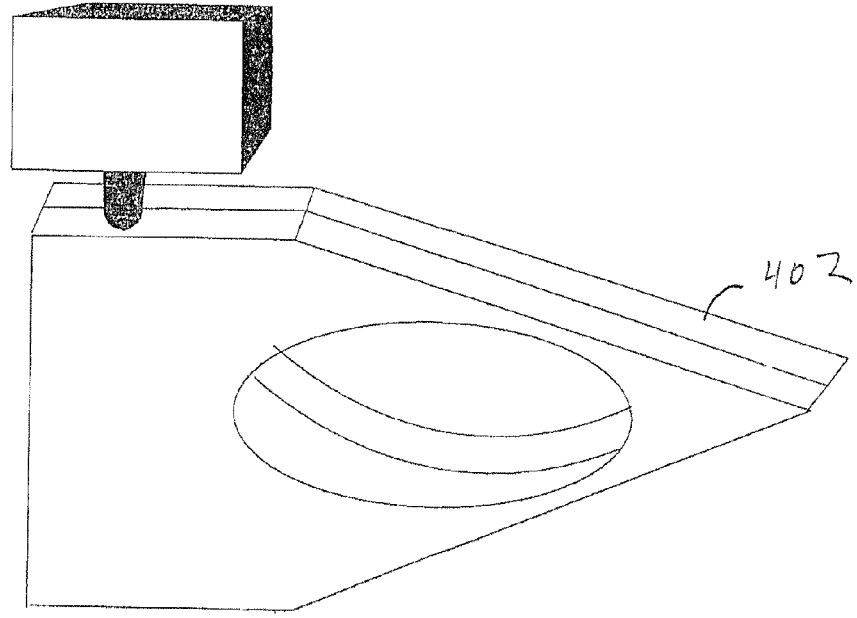
Figure 4C:
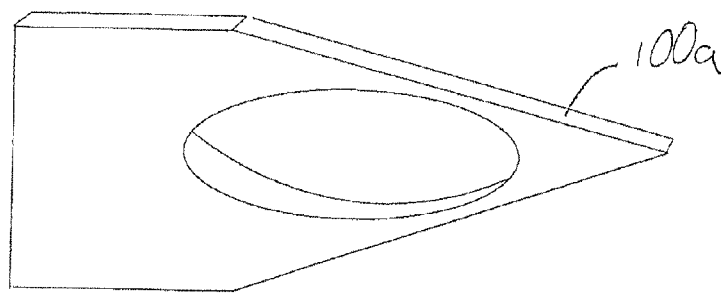

FIG. 4A depicts a method of forming a microneedle 100 using an injection molding technique according to an illustrative embodiment of the invention. The first step, depicted in FIG. 4A, includes providing a microneedle injection mold 402. The microneedle injection mold 402 can be formed using one or more of the microfabrication processes mentioned above. The interior of the microneedle injection mold 402 includes the relevant features of the microneedle 100. In the second step, depicted in FIG. 4B, a molten material, for example, a molten metal or plastic, is injected into the microneedle injection mold 402. After the molten material solidifies, the microneedle injection mold 402 is opened yielding the microneedle 100a depicted in FIG. 4C.

Figure 5A:
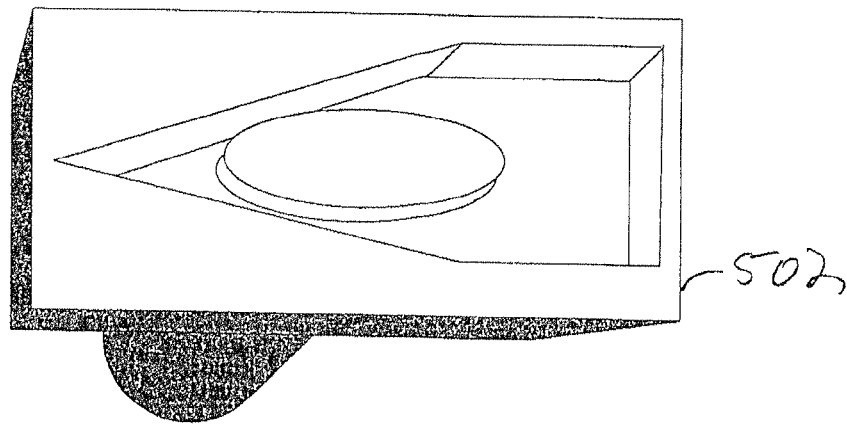
FIGS. 5A through 5C depict a method of forming a microneedle with an integrated drug reservoir using a stamping process according to an illustrative embodiment of the invention.
Figure 5B:
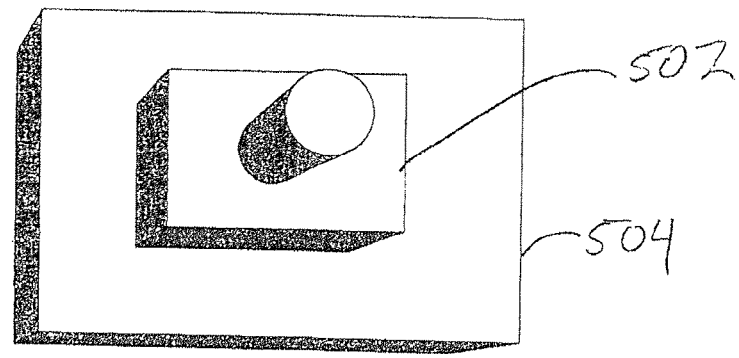
Figure 5C:
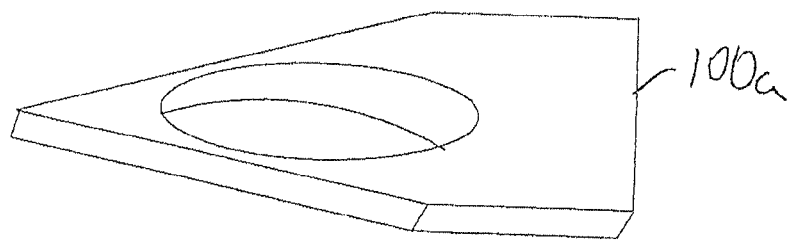

In similar methods, the microneedle injection mold 402 is formed from a transparent material. Light sensitive material is injected into the microneedle injection FIGS. 5A-5C depict a method of forming a microneedle 100 with an integrated reservoir 102 using a stamping process according to one illustrative embodiment of the invention. The first step, depicted in FIG. 5A includes providing a microneedle stamping mold 502. As with the microneedle injection mold 502 described with respect to FIG. 4A, the microneedle stamping mold 502 can be fabricated using one or more of the microfabrication techniques described above. As depicted in FIG. 5B, the microneedle stamping mold 502 is then stamped into the material 504 being used to form the microneedle 100. The material may be heated to a semi-solid or liquid state prior to stamping. If the material is heated prior to stamping, the material is allowed to cool before the microneedle stamping mold 502 is removed. After the microneedle stamping mold 502 is removed, excess material, if any, is removed, resulting in the microneedle 100 with an integrated reservoir 102 depicted in FIG. 5C. The stamping process can be used to form a strip or a sheet of microneedles. In addition, a substrate can be processed in a reel-to-reel fashion resulting in a continuous chain of microneedles.

In additional implementations of the methods described in relation to FIGS. 4A-5C, microneedles 100 can be formed using a multi-step process that may include both injection molding and stamping steps. For example the exterior shape of the microneedle 100, i.e., the microneedle 100 without a reservoir 102, is formed using injection molding or a first stamping step. Subsequently, a stamp may puncture the microneedle 100 to form the integrated reservoir 102.

Figure 6A:
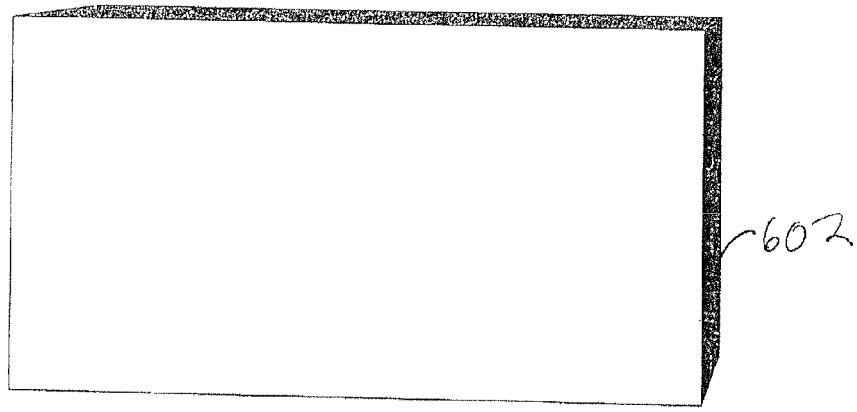
FIGS. 6A through 6C depict a method of forming a microneedle with an integrated drug reservoir using a chemical etching technique according to an illustrative embodiment of the invention.
Figure 6B:
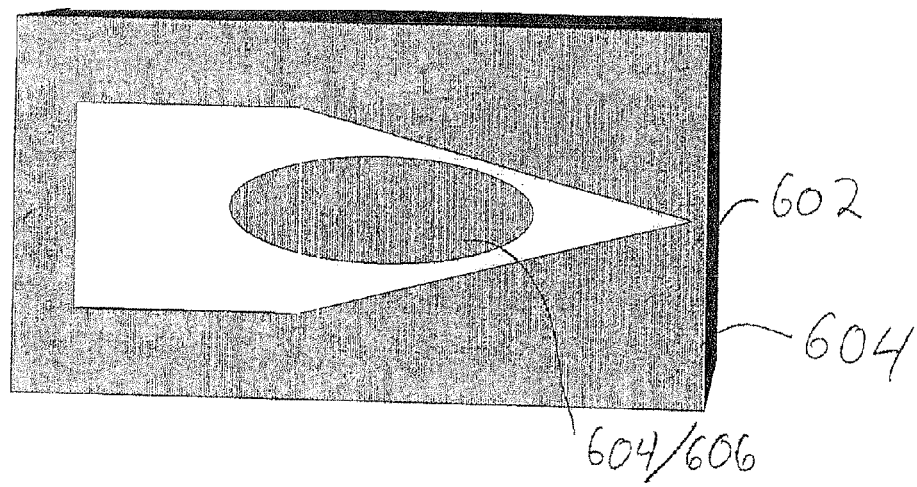
Figure 6C:
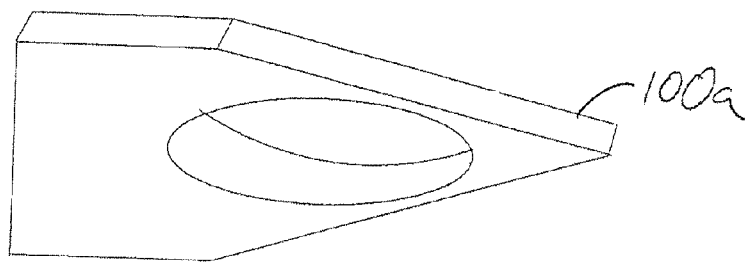

FIGS. 6A-6C depict a method of forming a microneedle 100 with an integrated agent reservoir 102 using an etching process according to an illustrative embodiment of the invention. A substrate 602 is provided from which the microneedle 100 is to be formed, as depicted in FIG. 6A. The substrate 602 may formed from a semiconductor material, such as silicon oxide, or any other semiconductor material suitable for insertion into a patient. FIG. 6B illustrates the application to the substrate 602 of a mask 604 defining the features of the microneedle 100. For example, the mask includes a reservoir portion 606. The chemical composition of the mask 604 depends upon the chemistry being used in the etch. Such mask/etch chemistry combinations are well known in the art of semiconductor substrate processing. See, e.g., Jansen, et al., "The Black Silicon Method IV: The Fabrication of Three-Dimensional Structures in Silicon with High Aspect Ratios for Scanning Probe Microscopy and Other Applications," IEEE Proceedings of Micro Electro Mechanical Systems Conference, pp. 88-93 (1995). In the sample illustrated in FIGS. 6A-6C, reactive ions etch away portions of the substrate 602 not protected by the mask 604, thereby yielding the microneedle 100 depicted in FIG. 6C. Etching can be used to multiple microneedles 100 at the same time. For example, masks corresponding to multiple microneedles 100 can be deposited linearly or in two dimensions across a substrate.

In other embodiments, the etching process includes a wet chemical etch or a combination of wet and dry etching. For example, in a first step, the process includes applying a first mask 604 corresponding to the exterior outline of the microneedle 100. A dry etch removes the unmasked material of the substrate 604. Subsequently, the process includes applying a second mask 604 leaving an area of the microneedle 100 exposed for forming the integrated agent reservoir 102. Various etching methods and etching times are then employed to form the reservoir 102.

The processes described above with respect to FIGS. 4A-6C can also be used to form microneedle arrays 200. In particular, the one-dimensional microneedle array 200c can readily be formed using a dry etching technique by applying a mask corresponding to the entire array shape.

Figure 7A:
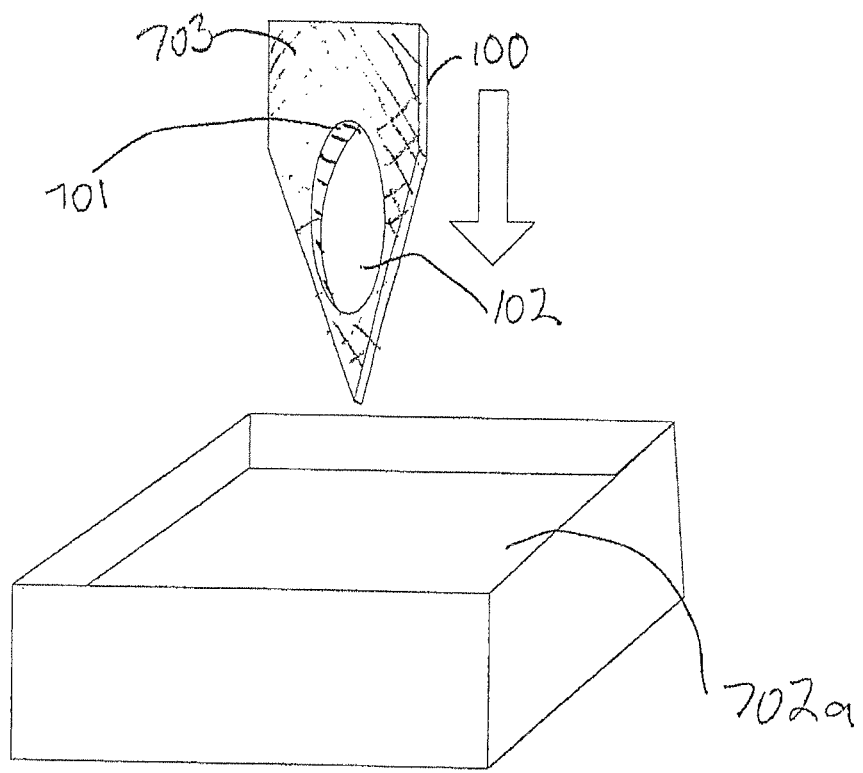
FIGS. 7A and 7B depict two methods of filling microneedle integrated agent reservoirs according to two embodiments of the invention.
Figure 7B:
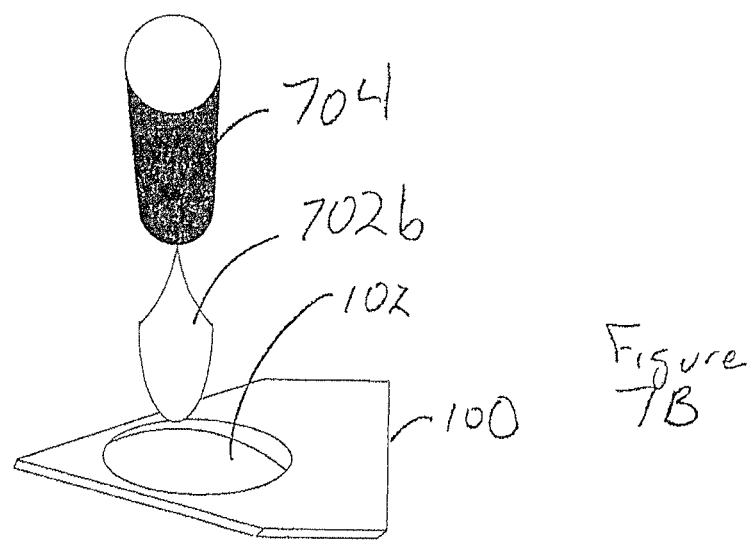

FIGS. 7A and 7B depict methods of filling integrated reservoirs 102 according to illustrative embodiments of the invention. The integrated reservoirs 102 can be either wholly or partially filled. In FIG. 7A, the integrated reservoirs 102 are filled using a dip process. The dip process includes physically dipping a microneedle 100 into a solution 702a of water or other solvent, which includes the agent 202. The solution can be either in a liquid or semi-solid gel-like state. The dipping process is well suited for filling one- and two-dimensional microneedle arrays 200. As described with respect to FIG. 3, the interior surface of the integrated reservoir 102 can be coated with a hydrophilic compound 701 while the remaining surface area of the microneedle 100 can be coated with a hydrophobic compound 703. As a result of the coatings and surface tension forces, when the microneedle 100 is removed from the solution, a volume of the aqueous solution 702a remains within the agent reservoir 102 but the remaining surface area of the microneedle 100 is substantially free of the aqueous solution 702a. In alternative embodiments, no coatings are applied, and residual aqueous solution 702a falls from the microneedle 100 due to gravity, while the integrated reservoir 102 remains filled due to surface tension forces.

FIG. 7B depicts a deposition reservoir filling process according to an illustrative embodiment of the invention. The process includes providing a microneedle 100 with an integrated reservoir 102. A dispensing device 704 (e.g., a micropipette or a syringe) deposits a predetermined volume of an aqueous solution 702b including the desired agent 202 into the integrated reservoir 102. The aqueous solution 702b dries or forms a gel within the integrated reservoir 102. As described above, the exterior surfaces of the microneedle 100 and the surfaces of the integrated reservoir 102 may be coated with hydrophobic and hydrophilic compounds to aid in the deposition process.

When depositing agents 202 into one-dimensional microneedle arrays 200c, the process may include multiple dispensing devices 704 corresponding to each microneedle 100 or to subsets of microneedles in the one-dimensional array. The multiple fluid dispensing devices 704 may all hold the same agent, or they may hold different agents. Microneedles 100 can be filled prior to attachment to a substrate or to other microneedles, or they may be filled subsequent to such attachment.

FIGS. 8A-9C depict methods of administering agents 202 using a microneedle 100 having an integrated agent reservoir 102 according to illustrative embodiments of the invention. For illustrative purposes, the biological barrier illustrated in the figures is the skin of a patient. The illustrated methods also apply to administering agents across other biological barriers. FIGS. 8A-8C depict three steps of administering an agent 202 using a microneedle 100a that does not have a depth guard 106, while the microneedle 100b in FIGS. 9A-9C has a depth guard 106. While the FIGS. 8A-9C depict transdermal delivery using single microneedles 100a and 100b, the methods illustrated therein also apply to transdermal delivery using microneedle arrays 200.

As depicted in FIG. 8A, an exemplary administration process includes providing a microneedle 100a having an integrated reservoir 102 filled with an agent 202. A microneedle applier (e.g., a patient, doctor, nurse, certified nurse's assistant, etc.) then applies the microneedle 100a to the skin 802 of the patient such that the microneedle 100a pierces the skin 802. The microneedle 100a may be applied manually or by using an impacting device which forces the microneedle 100a against the skin. Upon application, the microneedle 100a extends to a depth great enough such that the integrated reservoir 102 is located beneath the surface of the skin 802, but not deep enough to trigger a pain response in the patient, as depicted in FIG. 8B. The bloodstream of the patient absorbs the agent 202 in the agent reservoir 102, as depicted in FIG. 8C.

FIGS. 9A-9C are similar to FIGS. 8A-8C, though the microneedle 100b in FIGS. 9A-9C includes a depth guard 106. Thus, when the microneedle applier applies the microneedle 100b to the skin 902 of the patient, the microneedle 100b pierces the skin 902 to the depth at which the depth guard 106 rests upon the surface of the skin 902. As with the method illustrated in FIGS. 8A-8C, this depth is great enough that the integrated reservoir 102 sits beneath the surface of the skin 902 and shallow enough such that the application of the microneedle 100b does not trigger a pain response in the patient. As depicted in FIG. 9B, the depth guard 106 also prevents the wider base element 104 from expanding the puncture wound 904 caused by the application of the microneedle 100b.

FIGS. 10A-10E depict a medical device 1000 incorporating a microneedle 1002 with an integrated agent reservoir 1004 and an external reservoir 1006, and a method of using the same, according to an illustrative embodiment of the invention. The medical device 1000 includes a external reservoir 1006 storing at least one agent 1008. The microneedle 1002 is retractably mounted to the interior of the external reservoir 1006 such that the integrated agent reservoir 1004 of the microneedle 1002 can be withdrawn into the interior of the exterior reservoir 1006 and such that it can be forced out of the exterior reservoir 1006. The exterior reservoir 1006 is sealed such that the microneedle 1002 can move back and forth through the seal 1010 without the agent 1008 leaking from the external reservoir 1006.

Figure 10A:
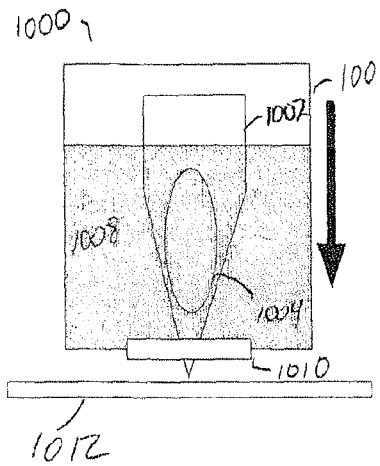
FIGS. 10A-10E depict a medical device incorporating a microneedle with an integrated agent reservoir and an external reservoir, and a method of using the same, according to an illustrative embodiment of the invention.
Figure 10B:
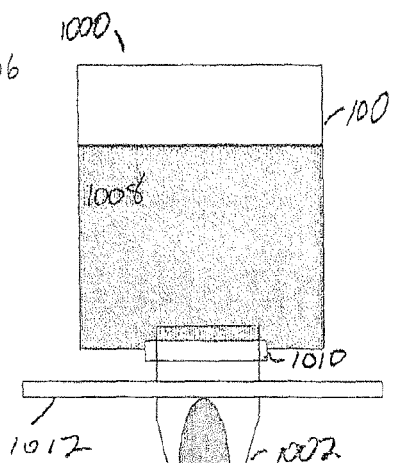
Figure 10C:
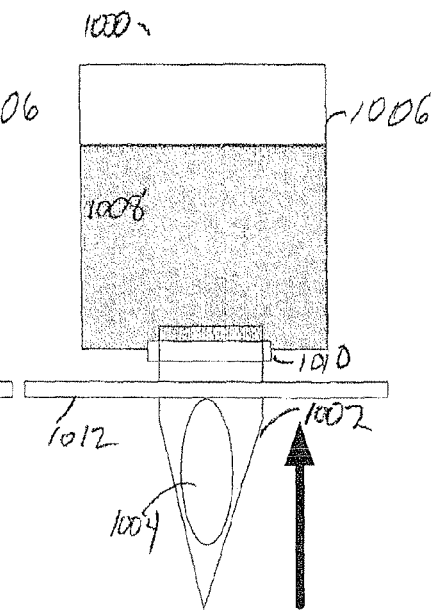
Figure 10D:
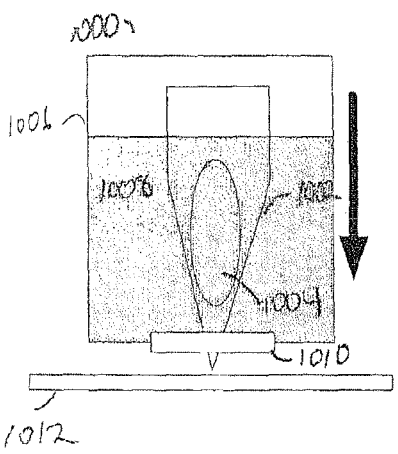
Figure 10E:
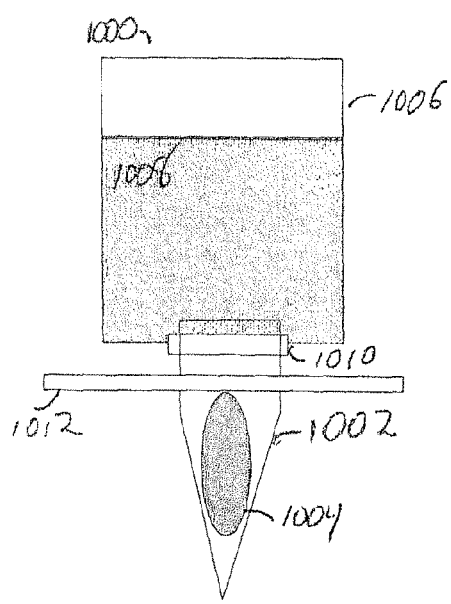

In operation, the microneedle 1002 begins in a retracted position, as depicted in FIG. 10A, such the integrated reservoir 1004 is positioned within the external reservoir 1006 and is exposed to the agent 1008. The medical device 1000 then forces the microneedle 1002 out of the external reservoir 1006 and through a biological barrier 1012, as depicted in FIG. 10B. A volume of agent 1008 remains within the integrated reservoir 1004 of the microneedle 1002 as a result of capillary forces, thereby transporting the agent 1008 across the biological barrier 1012. After a predetermined time, during which the agent 1008 in the integrated reservoir 1004 is absorbed into the target biological tissue, the microneedle 1002 is withdrawn to the initial position (see FIG. 10C) such that the integrated reservoir 1004 fills with an additional volume of the agent 1008. The process then repeats (see FIGS. 10D and 10E).

This retractable microneedle medical device 1000 can be used in situations in which an agent is administered over a prolonged period of time. For example, the device 1008 can be implanted within a patient, allowing continuous internal administration of accurately dosed agents without the need for external intervention.

The invention may be embodied in other specific forms without departing from the spirit or essential characteristics thereof. The foregoing embodiments are therefore to be considered in all respects illustrative, rather than limiting of the invention.

What is claimed is:

1. A method of manufacturing a device for delivering an agent across a biological barrier comprising:

providing a first microneedle having a first integrated reservoir which is an opening through the entirety of the width of the first microneedle, wherein the first microneedle extends from a first substrate, wherein a first depth guard extends from the first substrate, and wherein the first microneedle, the first substrate, and the first depth guard are integrally formed as a continuous single unit; and filling the first integrated reservoir with an agent by selectively depositing a predetermined volume of the agent into the first integrated reservoir utilizing a micropipette or a syringe, such that the agent is contained predominantly within the interior volume of the microneedle.

2. The method of manufacturing a device for transdermal delivery of an agent of claim 1 wherein filling the integrated agent reservoir comprises applying a hydrophilic compound to the interior of the integrated reservoir and applying a hydrophobic compound to a remainder of the microneedle.

3. The method of manufacturing a device for transdermal delivery of an agent of claim 1 further comprising providing a second microneedle having a second integrated reservoir which is an opening through the entirety of the width of the second microneedle wherein the second microneedle extends from a second substrate, wherein a second depth guard extends from the second substrate, and wherein the second microneedle, the second substrate, and the second depth guard are integrally formed as a continuous single unit; and filling the second integrated reservoir with an agent by selectively depositing a predetermined volume of the agent into the first integrated reservoir utilizing a micropipette or a syringe, such that the agent is contained predominantly within the interior volume of the microneedle.

4. The method of manufacturing a device for delivering an agent across a biological barrier of claim 1, wherein the first integrated reservoir comprises between about 50% - 70% of the volume of the first microneedle.

* * * * *